US005310545A

United States Patent [19]

Eisen

[11] Patent Number: 5,310,545
[45] Date of Patent: May 10, 1994

[54] METHOD OF TREATMENT USING MOUTHWASHES CONTAINING STEROIDS AND ANTIFUNGAL AGENTS AND COMPOSITIONS OF MATTER

[76] Inventor: Drore Eisen, 6720 E. Beechlands Dr., Cincinnati, Ohio 65237

[21] Appl. No.: 6,287

[22] Filed: Jan. 15, 1993

Related U.S. Application Data

[63] Continuation-in-part of Ser. No. 963,485, Oct. 21, 1992, which is a continuation-in-part of PCT/US92/02806, Apr. 10, 1992, and Ser. No. 802,646, Dec. 9, 1991, abandoned, which is a continuation-in-part of Ser. No. 683,380, Apr. 11, 1991, abandoned.

[51] Int. Cl.$^5$ .................... A61K 7/28; A01N 45/00
[52] U.S. Cl. ........................ 424/49; 514/171
[58] Field of Search ............... 514/171; 424/49

[56] References Cited

PUBLICATIONS

United States Pharmacopeia, 1980, p. 563.
Rothwell et al., Special Care in Dentistry, Palliation of Radiation-related Mucositis, Jan.-Feb. 1990, pp. 21-25.
Merck Index, entries 213, 1202, 2361, 2362, 2412, 6658, 6692, 9511; 1989.
Goodman et al., The Pharmacological Basis of Therapeutics, MacMillan, 1975, p. 1491.

*Primary Examiner*—Marianne M. Cintins
*Assistant Examiner*—Rebecca Cook
*Attorney, Agent, or Firm*—Glenna Hendericks; Stephen Gates

[57] ABSTRACT

Compositions used to treat inflammatory diseases of the mouth contain anti-inflammatory steroids in combination with antifungal drugs in an aqueous medium as a mouthwash. Swishing for three to five minutes, then expectorating the mouthwashes results in maintenance of contact of the active agents with the oral cavity surfaces for a longer time than would application of gels containing those agents. The mode of application is simple and is not repugnant to the patient as is the application of creams, gels, or ointments.

20 Claims, No Drawings

METHOD OF TREATMENT USING MOUTHWASHES CONTAINING STEROIDS AND ANTIFUNGAL AGENTS AND COMPOSITIONS OF MATTER

This application is a continuation-in-part of U.S. patent application Ser. No. 07/963,485, filed Oct. 21, 1992, which is a continuation-in-part of PCT application PCT/US92/02806, filed Apr. 10, 1992, and of U.S. patent application Ser. No. 07/802,646 filed Dec. 9, 1991, now abandoned, which is a continuation-in-part of U.S. patent application Ser. No. 07/683,380, filed Apr. 11, 1991, now abandoned.

FIELD OF THE INVENTION

The invention is related to treatment of inflammatory diseases of the mouth using anti-inflammatory steroids in combination with antifungal drugs in an aqueous medium as a mouthwash.

BACKGROUND OF THE INVENTION

The treatment of inflammatory diseases of the mouth is difficult. Patients so afflicted often require treatment with agents that are potentially toxic when given systemically to control the disease activity. Moreover, diseases such as oral lichen planus, pemphigus, pemphigoid, aphthous stomatitis, erythema multiforme, and idiopathic stomatitis are disorders in which spontaneous remissions are rare. Means of treating such diseases without undue exposure of the patient to systemic effects of powerful therapeutic agents is desirable.

Treatment with topical corticosteroids as presently formulated and administered has significant limitations. Existing commercially available compositions are usually supplied as creams, gels, or ointments that are intended for cutaneous applications. Such preparations are not readily acceptable to patients for use on the mucosa. The prior art compositions must be applied frequently (up to six times a day). Furthermore, the compositions are not readily applied to the areas of the oral cavity that are difficult to reach. Furthermore, treatment with steroids causes increased susceptibility to fungal infections of the mouth. This complication is especially common in patients suffering from oral lichen planus, a condition in which Candida is found to colonize mouth lesions in 25% of the patients.

Aqueous preparations of steroids are known. Kenalog (TM) 10 Injection is an aqueous suspension used for intradermal, intra-articular, and intrabursal administration. The suspension is not appropriate for use intravenously or intramuscularly, and there is no suggestion that the suspension can be used as a mouthwash or swish for treatment of inflammatory diseases of the oral cavity. Aristospan (TM) is also used as a suspension for intralesional administration and is available as a cream for topical application. Similarly, Kenalog-H (TM) cream is applied topically to the skin. Use of these preparations has an increased susceptibility of the patient to fungal infections as an untoward effect. A dermatological cream preparation containing an antifungal, nystatin, and a steroid, triamcinolone acetonide, is available under the trade name Mycolog II. Being a cream preparation, it is not appropriate for use as a mouthwash. Preparations containing a suspension of nystatin for use as a swish (mouthwash) are available. However, those preparations do not contain any anti-inflammatory steroid as an active agent.

No teaching of use of mouthwashes containing both antifungal agents and anti-inflammatory agents has been found in the patent literature. Segal, et al, in U.K. Patent Application GB 2,167,296 describe a variety of pharmaceutical compositions containing glycyrrhizin for topical applications. That patent publication indicates that the glycyrrhizin, a necessary component of the compositions taught therein, formed stable aqueous gels. A gel containing triamcinolone for treatment of oral ulcerations is described in one example. In another example a gel containing nystatin for treating oral candidiasis is described. U.S. Pat. No. 4,101,652 to Bonati teaches complexes of saponins with sterols for use in treating inflammation. The complex having a saponin as an essential moiety is necessary to that invention. Although use of the complexes in dentifrices is disclosed, no teaching of preparations for use as mouthwashes is seen therein. U.S. Pat. No. 4,933,172 to Clark, et al. teaches the nonsteroidal anti-inflammatory agent 2-(2,6 dichloro-3 methylphenylamino) benzoic acid for use in treating gingivitis. One of the formulations taught is a mouthwash. U.S. Pat. No. 4,835,142 to Suzuki, et al. describes powdery compositions for application to the mucosa of the oral or nasal cavity. U.S. Pat. No. 4,782,047 to Benjamin, et al. teaches use of anti-inflammatory steroids as nasal sprays. No method for treating oral infections using mouthwashes is disclosed therein.

R. A. Cawson ("Treatment of Oral Lichen Planus with Betamethasone", *British Medical Journal*, (Jan. 13, 1968)) teaches the use of betamethasone pellets to treat oral lichen planus. Use of hydrocortisone pellets was also tried. The betamethasone pellets were efficacious. Hydrocortisone pellets were rarely effective, even when combined with tetracycline mouthwashes.

Rothwell and Spektor ("Palliation of Radiation-related Mucositis", *Special Care in Dentistry*, (January-February 1990)) discloses a method of treating patients undergoing irradiation therapy comprising prophylactic use of mouth rinse with a preparation containing tetracycline, 500 mg; nystatin, 1,200,000 U; hydrocortisone, 100 mg; and diphenhydramine elixir, 10 ml. to make a solution of 25 ml. It is taught that tetracycline is unstable in solution and was, therefore, dispensed as a separate solution. It is not clear if the tetracycline was mixed with the other active agents just before using the rinse. However, the method taught therein was not used to treat existing, chronic inflammatory problems such as oral lichen planus.

SUMMARY OF THE INVENTION

The object of the present invention is to provide a means of treating patients suffering from inflammatory conditions of the mouth using anti-inflammatory steroids in aqueous preparations that can be swished and expectorated as a mouthwash. Such therapy allows direct contact of the medication with the diseased mucous membranes and contacts areas of the oral Cavity that usually are not reached with application of creams, gels, or ointments.

It is also an object of the invention to provide a method of treating patients suffering from inflammatory conditions of the oral cavity using compositions containing both anti-inflammatory steroids and antifungal agents in liquid aqueous preparations that can be swished and expectorated. The combination of active agents alleviates the inflammatory condition while inhibiting the growth of Candida species. The use of such mouthwashes results in efficient application Of both agents to all of the surfaces of the oral cavity, including areas that are not readily reached by application of gels, creams, or ointments.

Swishing for three to five minutes and then expectorating the aqueous anti-inflammatory-containing preparation results in maintenance of contact of the active agents with the oral cavity surfaces for a longer time than would application of gels containing those agents. The mode of application is simple and is not repugnant to the patient as is the application of creams, gels, or ointments.

DETAILED DESCRIPTION OF THE INVENTION

It is now possible, using the methods of the invention, to provide treatment to patients suffering from inflammatory conditions of the mouth in a manner that is effective, efficient, and results in minimal undesirable side effects. It has been found that patients suffering from such conditions may be treated using liquid aqueous preparations containing steroids as a mouthwash. Preferred mouthwashes contain, in addition to the steroids, antifungal agents. Treatment using the method of the invention is far more acceptable to patients than the use of creams, gels, or ointments. Furthermore, treatment using a mouthwash as a swish results in far better exposure of the entire oral cavity to the active agents.

The compositions used as mouthwashes preferably should be in the acidic range since most of the steroids and antifungal agents are more soluble in acidic preparations. A pH of 3.5 to 7 is desirable, with a pH of 4 to 6.5 being more preferable. A preparation having a pH of less than 4 would be likely to cause a stinging sensation. Steroids and antifungal agents are usually less soluble at pH higher than 7. Furthermore, at higher pH the preparations are often unpleasant to use. The active agents need not be in solution to be effective. The active agents may be present wholly or in part as suspensions in aqueous solutions used as carriers to provide liquid compositions. The preparations are buffered as necessary to provide the appropriate pH, as taught herein.

Anti-inflammatory steroids are classified according to anti-inflammatory efficacy of the preparation or according to relative effectiveness of the particular active agent used. (i.e., How much active agent is required to obtain a given effect?) Stoughton and co-workers, assigning efficacy to each preparation, assign a low efficacy to some preparations of hydrocortisone. A second method of classification ranking relative anti-inflammatory potency ranks anti-inflammatory agents in relation to the amount of agent needed to obtain a given anti-inflammatory effect wherein the more effective agents have a higher number assigned with a ranking of one given to hydrocortisone. Hydrocortisone at a ranking of 1 is listed as requiring an approximate dosage of 20 mg. while prednisolone, which provides equivalent anti-inflammatory effect using a dosage of 5 mg. is assigned a relative anti-inflammatory potency of 4 and betamethasone, with 0.75 mg. required to obtain equivalent anti-inflammatory effect, is assigned a relative anti-inflammatory potency rating of 25. (See Goodman and Gilman, *The Pharmacological Basis of Theraoeutics,* (*Eighth Ed.*), Pergamon Press, New York (1990) *pp* 1447-51 and 573-6.)

Using the ranking of relative anti-inflammatory effect in relation to hydrocortisone described above, any agent having a relative anti-inflammatory effect in relation to hydrocortisone of 2.5 or above is deemed useful for the practice of the invention. More preferred anti-inflammatory agents are those having a relative anti-inflammatory effect of at least 5.

Other factors to be considered in choosing a particular anti-inflammatory agent include cost and absorption of the particular agent which would be important factors in selecting the particular steroid. Steroids particularly suggested for use in the method of the invention include, but are not limited to: triamcinolone and its derivatives (particularly the diacetate, hexacetonide, and acetonide), betamethasone and its derivatives (including particularly the dipropionate, benzoate, sodium phosphate, acetate, and valerate), dexamethasone and its derivatives (particularly the dipropionate and valerate), flunisolide, prednisone and its derivatives (particularly its acetate), prednisolone and its derivatives (particularly its acetate, sodium phosphate and tebutate), methylprednisolone and its derivatives (particularly its acetate and sodium succinate), fluocinolone and its derivatives (particularly the acetonide), diflorasone and its derivatives (particularly the diacetate), halcinonide, desoximetasone (desoxymethasone), diflucortolone and its derivatives (particularly the valerate), flucloronide (fluclorolone acetonide), fluocinonide, fluocortolone, fluprednidene and its derivatives (particularly the acetate), flurandrenolide (flurandrenolone), clobetasol and its derivatives (particularly the propionate), clobetasone and its derivatives (particularly the butyrate), alclometasone, flumethasone and its derivatives (particularly the pivalate), fluocortolone and its derivatives (particularly the hexanoate), amcinonide, beclometasone and its derivatives (particularly the dipropionate), fluticasone and its derivatives (particularly the propionate), difluprednate, and desonide. The effective concentration of drug will vary with the active agent used. Concentrations will generally fall within the 0.01% to 1% range. For example, for betamethasone and its derivatives the preferred concentration is from about 0.01% to about 0.2% while the preferred concentration of triamcinolones is from about 0.025% to about 1%.

The preferred antifungal agents used in the method of the invention show great effectiveness against Candida species and are poorly absorbed from the mucosa of the intestinal tract. The preferred antifungal agents are poorly absorbed from the intestinal tract and include, but are not limited to, nystatin, clotrimazole, econazole, oxiconazole, ketoconazole, miconazole, ciclopirax olamine, amphotericin B, and sulconazole. Nystatin and clotrimazole are particularly preferred agents.

In addition to anti-inflammatory and antifungal agents, the aqueous preparation may contain buffers, surfactants, humectants, preservatives, flavorings, stabilizers (including antioxidants) colorants, and other additives used in preparations administered into the oral cavity. Of course other medicinal agents may be added for purposes of alleviating other undesirable conditions in the mouth. Such agents may include, for example, analgesics, antibacterial agents, and emollients.

Some of the appropriate buffer systems for use in practice of the invention include citric acid-citrate salts, acetic acid-acetate salts, and benzoic acid-benzoic salt systems. However, any buffer system commonly used for preparing medicinal compositions would be appropriate.

Flavorings used in the dentifrice art such as peppermint, citrus flavorings, berry flavorings, vanilla, cinnamon, and sweeteners, either natural or artificial, may be used in compositions of the invention.

While the vehicle used generally is primarily water, other vehicles may be present such as alcohols, glycols (polyethylene glycol or polypropylene glycol are examples), glycerin, and the like may be used to solubilize the active agents. Surfactants may include anionic, nonionic, amphoteric and cationic surfactants which are known in the art as appropriate ingredients for mouthwashes.

Suitable preservatives include, but are not limited to, butylated hydroxyanisole (BHA), butylated hydroxytoluene (BHT), benzoic acid, and ascorbic acid.

EXAMPLE 1

Preparations

A buffered solution containing benzalkonium chloride 0.02%, and 0.1% benzoic acid in water was adjusted to pH 4.5 with sodium benzoate. Betamethasone dipropionate and nystatin were added in sufficient quantities to provide a composition having a concentration of active agents in excess of 0.05% of betamethasone dipropionate and 100,000 units nystatin per ml. The pH was again adjusted to 4.5 and sufficient buffered solution added to provide a composition having 0.05% betamethasone dipropionate and nystatin 100,000 units per ml. (A dose for swishing is 5 ml.)

The aqueous preparation was placed in sealed containers containing 5 ml each. The patient was instructed to use one container full three times daily at least three hours before the next meal. Before use, the teeth were to be cleaned and the mouth rinsed. The preparation was to be swished around in the mouth for at least 3 minutes, then expectorated. Nothing was to be taken by mouth for at least 30 minutes after using the mouth wash.

EXAMPLE 2

A composition was prepared in the manner disclosed in Example 1. The active anti-inflammatory agent used was triamcinolone added in an amount to provide a final product having triamcinolone 0.1% and nystatin 100,000 units per ml. The composition was packaged in individual doses of 5 ml. in sealed containers. Instructions for use are the same as those for the composition of Example 1.

EXAMPLE 3

A mouthwash is prepared as indicated in Example 1. However, the preparation is packaged in a bottle containing multiple doses. The patient is instructed to use one teaspoon of fluid three times daily at least three hours before the next meal. Before use, the teeth should be cleaned and the mouth rinsed. The preparation is to be swished around in the mouth for at least 3 minutes, then expectorated. Nothing is to be taken by mouth for at least 30 minutes after use of the mouthwash.

EXAMPLE 4

A mouthwash composition is prepared by the method used in Example 1 except that the active agents are replaced with clobetasol propionate 0.05% as the anti-inflammatory steroid and, as the antifungal agent, oxiconazole nitrate 1%.

EXAMPLE 5

A mouthwash composition is prepared by the method of Example 1 except that the active agents are replaced with the steroid alclometasone dipropionate 0.05% and, as the antifungal agent, oxiconazole nitrate 1%.

EXAMPLE 6

A mouthwash composition is prepared by the method of Example 1 except that the active agents are replaced with the steroid fluticasone propionate 0.05%.

EXAMPLE 7

A mouthwash composition was prepared by the method of Example 2 except that the concentration of triamcinolone was 0.5%. The nystatin dosage was 100,000 U/ml.

EXAMPLE 8

A mouthwash composition was prepared in accord with the method of Example 1 except that the antifungal agent was clotrimazole 1%.

COMPARATIVE DATA

Mouth washes of the invention were compared for effectiveness with known commercial formulations. Each of the patients were first treated with the known formulations. In the patients tested, response to the prior art compositions was poor.

| | Patient #1 Diagnosis: Lichen planus Patient #2 Diagnosis: Pemphigoid | |
|---|---|---|
| | Response | |
| Drug | Pt. #1 | Pt. #2 |
| Mycolog II: | ± | 0 |
| Lotrasone: | + | + |
| Mouthwash of Example 2: | ++ | +++ |
| Mouthwash of Example 7: | ++++ | +++ |
| Mouthwash of Example 8: | ++++ | ++++ |

0: no improvement,
±: very slight improvement,
+: slight improvement,
++: moderate improvement,
+++: good improvement,
++++: excellent improvement.

The mouthwashes of the invention were then compared with the compositions of Rothwell, et al. Three patients were tested using the compositions of Rothwell to assure that any negative result was not a false negative. Comparison with results shown using compositions of the invention is shown below.

| | Diagnosis: Lichen planus |
|---|---|
| Drug | Response |
| Compositions of Rothwell containing hydrocortisone and tetracycline | 0/±/0 |
| Swish of 0.1% triamcinolone: 100,000 U/cc nystatin | +++/+++/+++ |
| Swish of 0.05% betamethasone: 1% clotrimazole | ++++/++++/++++ |

0: no improvement,
+: slight improvement,
++: moderate improvement,
+++: good improvement,
++++: excellent improvement As indicated above, the use of the swish in accord with the teachings of the specification provides therapeutic relief in the treatment of the Lichen planus of the mouth while the compositions taught in Rothwell were essentially ineffective. The data indicate clearly that the compositions of Rothwell are not equivalents of the compositions taught herein.

As indicated above, the use of the swish in accord with the teachings of this specification provides greatly increased therapeutic relief in the treatment of the cited inflammatory conditions of the mouth. Hence, it can be seen that the use of the liquid mouthwash preparation as described provides substantial benefit over use of prior art compositions.

While several useful anti-inflammatory compositions have been exemplified, it is understood that other anti-inflammatory steroids may be chosen from among those having a potency of >2.5 in relation to hydrocortisone and other antifungal agents, especially those that are poorly absorbed in the gastrointestinal tract, may be used in accord with the teachings of this disclosure without departing from the spirit of the invention.

The compositions of the invention containing anti-inflammatory agents and antifungal agents can be used for veterinary purposes as well. However, when so used the therapeutic composition would be sprayed into the oral cavity after the teeth of the animal have been cleaned. The animal would then be prevented from ingestion of food or water for about 30 minutes.

As is obvious to one of ordinary skill in the art, other additives, including other active agents, may be incorporated with the active agents of the invention as taught herein.

I claim:

1. A composition of matter having a pH of 3.5 to 7 comprising a liquid aqueous carrier containing as active agents an antifungal effective amount of at least one antifungal agent and an anti-inflammatory effective amount of at least one anti-inflammatory steroid having a relative anti-inflammatory potency of at least 2.5 when compared to hydrocortisone.

2. A composition of claim 1 having a pH of 4 to 6.5.

3. A composition of claim 2 wherein the anti-inflammatory steroid is selected from the group consisting of triamcinolone, betamethasone, flunisolide, prednisone, fluocinolone, diflorasone, halcinonide, desoximetasone, clobetasol, alclometasone, fluticasone, dexamethasone, prednisolone, methylprednisolone, fluocinolone, desoximetasone, diflucortolone, flucloronide, fluocinonide, fluocortolone, fluprednidene, flurandrenolide, clobetasone, flumethasone, fluocortolone, amcinonide, beclometasone, difluprednate and desonide.

4. A composition of claim 1 wherein the fungicidal antifungal agent is selected from the group consisting of nystatin, clotrimazole, econazole, oxiconazole, ketoconazole, miconazole, ciclopirax olamine, amphotericin B, and sulconazole.

5. A composition of claim 4 wherein the anti-inflammatory steroid is betamethasone dipropionate.

6. A composition of claim 4 wherein the anti-inflammatory steroid is triamcinolone.

7. A composition of claim 4 wherein the anti-inflammatory steroid is clobetasol propionate.

8. A composition of claim 4 wherein the anti-inflammatory steroid is alclometasone dipropionate.

9. A composition of claim 4 wherein the anti-inflammatory steroid is fluticasone propionate.

10. A composition of claim 1 wherein the antifungal agent is nystatin.

11. A composition of claim 1 wherein the antifungal agent is oxiconazole.

12. A composition of claim 1 wherein the antifungal agent is clotrimazole.

13. A composition of claim 3 wherein the antifungal agent is nystatin.

14. A composition of claim 3 wherein the antifungal agent is oxiconazole.

15. A composition of claim 3 wherein the antifungal agent is clotrimazole.

16. A composition of claim 4 wherein the steroid is triamcinolone.

17. A composition of claim 4 wherein the steroid is betamethasone dipropionate.

18. A composition of claim 4 wherein the steroid is clobetasol propionate.

19. A composition of claim 4 wherein the steroid is alclometasone dipropionate.

20. A composition of claim 4 wherein the steroid is fluticasone propionate.

* * * * *